United States Patent [19]

Bernhardt et al.

[11] Patent Number: 5,286,291
[45] Date of Patent: Feb. 15, 1994

[54] PIGMENTS CONTAINING CARBON BLACK

[75] Inventors: Klaus Bernhardt, Bross Umstadt; Gerhard Pfaff, Munster, both of Fed. Rep. of Germany

[73] Assignee: Merck Patent Gesellschaft mit beschrankter Haftung, Darmstadt, Fed. Rep. of Germany

[21] Appl. No.: 87,095

[22] Filed: Jul. 7, 1993

[30] Foreign Application Priority Data

Jul. 8, 1992 [DE] Fed. Rep. of Germany ....... 4222372

[51] Int. Cl.$^5$ ............................................... C09C 1/44
[52] U.S. Cl. .................................... 106/474; 106/418; 106/417; 106/475; 106/490
[58] Field of Search ............... 106/417, 418, 474, 475, 106/476, 490, 506

[56] References Cited

U.S. PATENT DOCUMENTS

| | | | |
|---|---|---|---|
| 4,076,551 | 2/1978 | Bernhard et al. | 106/474 X |
| 4,464,203 | 8/1984 | Belde et al. | 106/474 X |
| 4,724,005 | 2/1988 | Minten et al. | 106/475 |

*Primary Examiner*—Mark L. Bell
*Assistant Examiner*—Chris Gallo
*Attorney, Agent, or Firm*—Millen, White, Zelano, & Branigan

[57] ABSTRACT

The invention relates to a pigment containing carbon black having improved abrasion resistance comprising a platelet-shaped substrate coated with a metal oxide layer containing carbon black, wherein the carbon black is fixed on the substrate by means of an anionic or cationic and a nonionic surfactant and an organosilane compound.

18 Claims, No Drawings

PIGMENTS CONTAINING CARBON BLACK

BACKGROUND OF THE INVENTION

The invention relates to pigments containing carbon black and having improved abrasion resistance and to a process for their preparation.

It is known to achieve special color effects by incorporation of carbon black in pigments. However, the known processes have in some cases substantial disadvantages.

German Auslegeschrift 1,165,182 describes a complicated process by which the carbon black is formed by pyrolysis of organic compounds in the presence of the pigments to be coated. In this process, the carbon black is naturally precipitated in the presence of organic compounds only on the pigment surface. This smooths out the spaces between $TiO_2$ particles applied to a microsurface.

Some disadvantages of this complicated pyrolysis process are eliminated in German Patent 2,557,796. In the process described there, first a substrate dispersion is mixed with a carbon black dispersion. The addition of a metal salt solution under hydrolysis conditions results in precipitation of a metal hydroxide film containing carbon black on the substrate. The products prepared in this manner are separated off and dried at 110°–130° C. However, it has been found that the dried pigments are unsuitable for various areas of application, since their wear resistance is insufficient. This property is extremely desirable especially for incorporation in cosmetics.

In the processes disclosed in the prior art, precipitation of the carbon black is not quantitative, i.e., some of the carbon black is present on the pigment in agglomerated form, so that the pigments do not have good hiding power. The unprecipitated carbon black has to be removed by sedimentation, which is time-consuming and cost-intensive.

A further disadvantage is the often observable bleeding of the carbon black upon suspension of the pigments in organic solvents for preparing coating systems.

SUMMARY OF THE INVENTION

Accordingly, there was a need for preparing pigments containing carbon black and having improved abrasion resistance and bleeding resistance without the need for a large technical expenditure. This object has been achieved by the present invention.

Surprisingly, it has been found that pigments containing carbon black and showing quantitative carbon black inclusion and thus improved abrasion resistance and bleeding resistance are obtained by coating a platelet-like substrate with a film (i.e. a layer) containing carbon black, and optionally a metal oxide, and being doped with an anionic or cationic and a nonionic surfactant and an organosilane compound. In other words, the invention involves a pigment containing carbon black comprising a platelet-shape substrate coated with a metal oxide layer containing carbon black, wherein the carbon black is fixed on the substrate by means of an anionic or cationic and a nonionic surfactant and an organosilane compound. By "fixed" is meant that the carbon black particles are attracted to and retained on the substrate due at least in part to the action of the surfactants.

Apparently, the carbon black particles covered by an anionic coating are attracted, by virtue of their negative charge, towards the substrate film which is positively charged under acidic conditions, while the nonionic surfactant prevents agglomeration of the carbon black particles. In the case of carbon black particles covered by a cationic coating, deposition takes place analogously as if the substrate surface is negatively charged. Bleeding of the carbon black is largely reduced, on the one hand, by the small carbon black particle size and, on the other hand, by the organosilane compound.

Accordingly, the invention relates to pigments containing carbon black and having improved abrasion resistance, a platelet-like (e.g., platelet-shaped) substrate being coated with a metal oxide film containing carbon black, characterized in that the film containing carbon black is fixed by means of an anionic or cationic and a nonionic surfactant and an organosilane compound The invention also relates to a process for the preparation of pigments containing carbon black and having improved abrasion resistance, characterized in that an aqueous substrate suspension is prepared and preferably simultaneously either (a) a hydrolyzable metal salt solution;
(b) a carbon black dispersion containing an anionic or cationic surfactant;
(c) a carbon black dispersion containing a nonionic surfactant; and
(d) an organosilane compound or
(a) a hydrolyzable metal salt solution;
(b) a carbon black dispersion containing an anionic or cationic surfactant;
(c) an aqueous solution containing a nonionic surfactant; and
(d) an organosilane compound or
(a) a hydrolyzable metal salt solution;
(b) a carbon black dispersion containing a nonionic surfactant;
(c) an aqueous solution containing an anionic or cationic surfactant; and
(d) an organosilane compound are added, during which the pH of the substrate suspension is maintained in a range causing hydrolysis of the metal salt by simultaneous addition of a base or an acid, and in that, if desired, the process mentioned is followed by a further hydrolysis of metal salt but without readdition of carbon black, the substrate coated in this manner is separated off, and, if desired, washed, dried and calcined. These processes, and obvious variants thereof, yield pigments comprising one or more layers of carbon black combined with metal oxides, pigments comprising discrete layers of carbon black and layers of metal oxides and pigments comprising carbon black without metal oxide.

The pigments thus prepared no longer require sedimentation, in order to remove free carbon black.

The invention also relates to the use of the pigments according to the invention in formulations, such as varnishes, dyes, plastics and cosmetics.

The invention finally relates to formulations containing the pigments according to the invention.

Any platelet-like substrates can be coated by the process according to the invention.

Preferred substrates are layered silicates, platelet-like oxides or metal platelets and platelet-like materials coated with metal oxide. Mica, talc, kaolin, bismuth oxychloride or platelet-like iron oxide and mica coatings using colored or colorless metal oxides, such as $TiO_2$, $Fe_2O_3$, $SnO_2$, $Cr_2O_3$, ZnO and other metal oxides, alone or a mixture in a uniform layer or in subsequent layers, are particularly suitable. These pigments known as nacreous pigments are disclosed, for example, in German Patents and Patent Applications, 1,467,468, 1,959,998, 2,009,566, 2,214,545, 2,215,191, 2,244,298, 2,313,331, 2,522,572, 3,137,808, 3,137,809, 3,151,343, 3,151,354, 3,151,355, 3,211,602 and 3,235,017.

In order to prepare the pigments according to the invention containing carbon black, first an aqueous suspension of the substrate is prepared. A metal salt solution and the carbon black dispersions are then added preferably simultaneously but separately, during which the pH of the reaction mixture is maintained in a range causing hydrolysis of the metal salt by simultaneous addition of a base. This results in precipitation of the metal hydroxide and the carbon black particles, the latter in finely dispersed form, on the substrate surface. Preferably, simultaneously with the further addition of metal salt solution, the solution of an organosilane is metered in separately. It is also possible to use only one carbon black dispersion containing either anionic or cationic or nonionic surfactant and additionally one aqueous solution of the missing surfactant (anionic or cationic or nonionic). Furthermore, addition of the metal salt solution can also be interrupted during addition of the silane.

The individual process parameters for coating, i.e., for hydrolysis of the metal salt, are of conventional nature and described in detail, for example, in DE 2,557,796 (corresponding to U.S. Pat. No. 4,076,551). All further parameters, such as, for example, particle sizes, metal salt concentrations, temperatures and preferred embodiments can also be seen, for example, from DE 2,557,796.

If desired, the pigments according to the invention can also be recoated, in which it is however preferred not to add any additional carbon black. This makes it possible to selectively adjust the color of the pigments (the degree of blackness), thus giving new color effects.

After the product prepared in this manner has been separated off, washed and dried, the pigments, if desired, are calcined at 700°-900° C. in an $N_2$ stream. As a rule, the calcining temperature depends on the metal hydroxide and the thickness of the precipitated film; the calcining time can range from a few minutes to several hours but is preferably between 20 and 120 minutes.

An essential component of the coating agent is the carbon black mixture which is preferably composed of two carbon black dispersions of the same carbon black grade. However, it is also possible to work with only one carbon black grade, i.e., without a carbon black mixture, if the necessary surfactants are present.

Carbon black dispersion I contains an anionic or cationic surfactant, while carbon black dispersion II contains a nonionic surfactant. Carbon black dispersions I and II are mixed with water and are added simultaneously but separately together with the metal salt solution to the substrate suspension. It is also possible to work with only one carbon black dispersion. In the case where one carbon black dispersion containing an anionic or cationic surfactant is used, a nonionic surfactant must be added in addition Conversely, if a nonionic stabilized carbon black dispersion is used, an anionic or cationic surfactant must be used in addition. The carbon black dispersions can be prepared by dispersing carbon black, water and surfactant in water but it is also possible to use commercially available aqueous carbon black dispersions, for example those from Degussa, Germany, such as, for example, Derussol ®.

Selection of the carbon blacks or carbon black dispersions is not very critical. The primary particle size is preferably about 10–50 nm and in particular 10–25 nm. The amount of carbon black used ranges preferably from about 0.1 to 5.0% by weight, relative to the substrate, but is preferably 0.5 to 2.0% by weight. These values produce film thicknesses of up to 50 nm. In the case of higher film thicknesses, a larger amount of carbon black of up to 20% by weight, relative to the substrate, is used.

The proportion of carbon black in the pigments according to the invention is between 0.1 and 10% by weight, relative to the total pigment. Owing to the different substrates, the weight proportion of carbon black can vary very widely. For nacreous pigments, the carbon black content is in general between 0.2 and 5.0% by weight.

Overall, the carbon black dispersions contain preferably 0.1 to 10% by weight, preferably 0.1 to 3% by weight, of anionic or cationic and nonionic surfactants.

The weight ratio of anionic or cationic to nonionic surfactant is between 1:1 and 1:5. Virtually any known anionic, cationic and nonionic surfactant may be employed in the invention. Suitable anionic surfactants include carboxylates, isethionates, phosphate esters, sarcosinates, organic sulphates, sulphosuccinates, sulphosuccinamates and taurates. Suitable cationic surfactants include quaternary ammonium compounds, amine salts and imidazolium salts. Sulphonates are preferably used. Examples of nonionic surfactants which can be used include alkanolamides, amine oxides, derivatives of carbohydrates, ethoxylated alkanolamides, ethoxylated long-chain amines, ethylene oxide/propylene oxide copolymers, ethoxylates of fatty acids, sorbitan derivatives, ethylene glycol esters, propylene glycolesters, glycerine esters and polyglycerine esters and ethoxylated derivatives thereof, alkylamines and alkyl-imidazolines, ethoxylated oils and fats, alkylphenol ethoxylates and acetylenic surfactants, alcohol ethoxylates being preferred.

Bleeding of the carbon black is drastically reduced, on the one hand, by the small carbon black particle size and, on the other hand, by applying a silane to the pigment surface and, if desired, by reprecipitation of a metal salt, i.e., production of an additional (e.g., a top) metal oxide layer on the carbon black-containing pigment.

Suitable silane compounds include organosilanes of the formula $Y-(CH_2)_n-SiX_3$, in which Y is
$H_2N-$, 

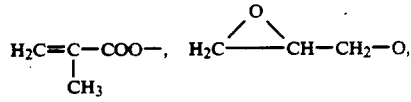

or 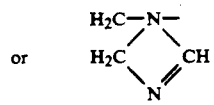

X is OR, Cl, or $-O-CO-CH_3$,
R is alkyl having 1–6 C atoms and
n is 0–3.

Preferably, amino silanes are used. The following silane compounds are also preferred:

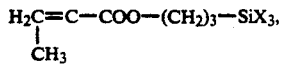

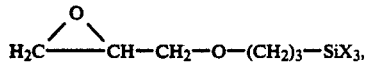

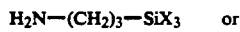

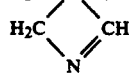

X is preferably alkoxy having 1-6 C atoms, especially methoxy and ethoxy.

The proportion of silanes is preferably 0.5-10% by weight, more preferably 1-3% by weight, relative to the total pigment.

The pigments prepared according to the invention are almost completely abrasion-resistant, enabling them to be used for a wide range of purposes, in particular for automotive coatings, printing inks and in cosmetics.

Bleeding of the carbon as a result of organic solvents can hardly be observed and disappears completely in the case of recoatings. Furthermore, the pigments according to the invention are distinguished by increased luster and also by their high hiding power. Moreover, the pigments are nonconductive and resistant to weathering.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire texts of all applications, patents, and publications, cited above and below, and of corresponding German Application P 42 22 372.5, filed Jul. 8, 1992, are hereby incorporated by reference.

EXAMPLES

Example 1

100 g of mica of particle size 5-25 μm are suspended in 2 l of water, and the suspension is heated to 75° C. A 0.009 molar $SnCl_4$ solution (2.99 g of $SnCl_4 \times 5\ H_2O$ in 75 ml of $H_2O$ and 7.5 ml of 5% HCl) are metered in over a period of 20 minutes. After addition is complete, the mixture is stirred for a further 10 minutes in order to complete the precipitation reaction. 150 ml of an aqueous $TiCl_4$ solution (385 g of $TiCl_4$/l of $H_2O$) and the carbon black dispersion (4.66 g of Derussol A and 8.12 g of Derussol A NI-61/1 (Degussa) in 150 ml of water) are added simultaneously but separately to the reaction mixture over a period of 1 hour.

The pH is kept constant during the addition at 1.8 with 32% NaOH solution. After complete addition of the carbon black dispersion and the $TiCl_4$ solution, another 100 ml of $TiCl_4$ solution are added dropwise to the reaction mixture. $TiCl_4$ solution and silane solution [3 g of Z 6020 (DAMO $H_2N-(CH_2)_2-NH-(CH_2)_3-Si(OCH_3)_3$) from Dow Corning in 150 ml of $H_2O$] are then metered in simultaneously but separately. After reaching the desired silvery color, addition of the $TiCl_4$ solution (a total of ~380 ml) is stopped. The mixture is then stirred for a further 0.5 hour. The pigment suspension is allowed to settle, and the supernatant is drained off after approximately 1.5 hours. Finally, the pigment is washed with water and dried at 120° C. for 16 hours.

The coated pigment contains 1.3% of $SnO_2$, 2% of carbon black, 3% of silane and 61.4% of $TiO_2$ and has a silver-grey color.

Example 2

100 g of mica of particle size 10-60 μm are suspended in 2 l of water, and the suspension is heated to 75° C. The $SnCl_4$ solution (2.3 g of $SnCl_4 \times 5\ H_2O$ in 50 ml of $H_2O$ and 5 ml of 5 % HCl) is metered into the pigment suspension over a period of 15 minutes. After addition is complete, the mixture is stirred for a further 10 minutes. Analogously to Example 1, 250 ml of $TiCl_4$ solution (385 g of $TiCl_4$/l of $H_2O$) and the carbon black dispersion (2.5 g of Derussol A and 7.05 g of Derussol A Nl-16/1 (Degussa) in 250 ml of $H_2O$) are then added simultaneously but separately to the reaction mixture. The pH is kept constant during the addition at 1.8 with 32% NaOH solution. After addition is complete, another 10 ml of $TiCl_4$ solution are added dropwise by themselves to the reaction mixture, and stirring is then continued for 5 minutes. 150 ml of silane solution (3 g of Z 6020 from Dow Corning in 150 ml of $H_2O$) are then added over a period of one minute, and the mixture is stirred for 5 minutes.

Coating using $TiCl_4$ solution is then continued until the desired silver color has been reached. (Total consumption of $TiCl_4$ solution: about 280 ml). The mixture is then stirred for a further 0.5 hour. The pigment suspension is allowed to settle, and the supernatant is drained off after about 1.5 hours and replaced by water. The aqueous pigment suspension is brought to a pH of 10.0 with 32% NaOH while stirring. After 15 minutes of stirring, the solution is filtered off with suction, and the finished pigment washed until salt-free. Finally, the pigment is dried at 120° C. for 16 hours, and 50 g of the pigment are then calcined at 850° C. in an $N_2$ stream for 45 minutes.

The coated pigment contains 1% of $SnO_2$, 1.5% of carbon black, 3% of silane and 44.5% of $TiO_2$ and has a silver-grey color.

Example 3

100 g of mica of particle size 10-60 μm are suspended in 2 l of water, and the suspension is heated to 75° C. The SnCl, solution (2.3 g of SnCl, × 5 $H_2O$ in 50 ml of $H_2O$ and 5 ml of 5% HCl) is metered into the pigment suspension over a period of 40 minutes. After addition is complete, the mixture is stirred for a further 10 minutes. 0.3 g of Brij 30 (nonionic surfactant from Th. Goldschmidt AG, Essen) is then added. 150 ml of an aqueous TiCl, solution (385 g of $TiCl_4$/l ) and the dilute carbon black dispersion (10 g of Derussol A (Degussa) diluted to 150 ml with $H_2O$) are then added simultaneously but separately to the reaction mixture over a period of 1 hour. The pH is kept constant during the addition at 1.8 with 32% NaOH. After addition is complete, another 10 ml of $TiCl_4$ solution are added dropwise to the reaction mixture, and stirring is continued for 5 minutes. 150 ml of silane solution (3 g of Z 6020 from Dow Corning in 150 ml of H₂O) are then added over a period of one minute, and the mixture is stirred for 5 minutes.

Coating using TiCl₄ solution is then continued until the desired silver color has been reached. (Total consumption of TiCl₄ solution: about 280 ml). The mixture is then stirred at room temperature for a further 0.5 hour. The pigment suspension is brought to a pH of 5–6 with 32% NaOH. After 5 minutes of stirring the pigment suspension is filtered with suction, and the finished pigment is washed until salt-free. Finally, the pigment is dried at 120°–140° C. for about 16 hours. 50 g of the product are calcined in an N₂ stream for 45 minutes at 850° C.

The coated mica contains 1% of SnO₂, 1.5% of carbon black, 3% of silane (Z 6020) and about 40% of TiO₂ and has a silver-grey color.

EXAMPLE 4

100 g of the silver-grey pigment prepared according to Example 3 are stirred in 2 l of water for 15 minutes and then allowed to settle overnight. The supernatant is drained off and replaced by 2 l of water. 1.4 l of TiCl₄ solution (384 g of TiCl₄/l of H₂O) are added dropwise to the pigment suspension over a period of 11 hours. The pH is kept constant during the coating at 1.8 with 32% NaOH. Upon reaching the desired green color, coating is stopped. The mixture is then stirred for a further 0.5 hour. Work up is carried out analogously to Example 3.

This gives pigments having a grey surface color and very distinct interference of high luster.

EXAMPLE 5

100 g of mica of particle size 10–60 μm are suspended in 2 l of water, and the suspension is heated to 75° C. SnCl₄ solution (2.3 g of SnCl₄ × 5 H₂O in 50 ml of H₂O and 5 ml of 5% HCl) is metered into the mica suspension over a period of 40 minutes. After addition is complete, the mixture is stirred for a further 10 minutes. 1200 ml of aqueous TiCl₄ solution *385 g of TiCl₄/l of H₂O) and a carbon black dispersion (50 g of Derussol A, diluted to 1200 ml with H₂O) are then added simultaneously but separately to the reaction mixture over a period of 9.5 hours. The pH is kept constant during the addition at 1.8 with 32% NaOH. After addition is complete, another 10 ml of TiCl₄ solution are added dropwise to the reaction mixture. After stirring for 5 minutes, 150 ml of silane solution (3 g of Z 6020 from Dow Corning in 150 ml of H₂O) are added over a period of one minute. The mixture is then stirred for 5 minutes. Coating using TiCl<solution is then continued until the desired green color has been reached. (Total consumption of TiCl₄ solution: 1400 ml). The further work-up is analogous to Example 3.

The coated mica contains 1% of SnO₂, 7.5% of carbon black, 3% of silane (Z 6020) and 200% of TiO₂ and has a green surface color of very distinct green interference.

EXAMPLES 6–10

100 g of mica of particle size 10–60 μm are suspended in 1 l of water, and the suspension is heated to 75° C. SnCl₄ solution (2.3 g of SnCl<x 5 H₂O in 50 ml of water and 5 ml of 5% HCl) is metered into the mica suspension over a period of 40 minutes. After addition is complete, the mixture is stirred for a further 10 minutes. 0.8 g of Brij 30 (nonionic surfactant from Th. Goldschmidt AG, Essen) is then added. 200 ml of an aqueous of an aqueous TiCl₄ solution (385 g of TiCl₄/l of H₂O) and a carbon black dispersion (10 g of Derussol A from Degussa, diluted with water to 200 ml) are then added simultaneously but separately to the reaction mixture. The pH is kept constant during the addition at 1.8 with 32% NaOH. After addition is complete, another 10 ml of TiCl₄ solution are added dropwise to the reaction mixture, with stirring for 5 minutes. 150 ml of silane solution are then added over a period of one minute, with further stirring for 5 minutes. The quantity of silane is in each case 3 g in 150 ml of water.

The following silanes are used:

Example 6: MEMO $H_2C=C(CH_3)-COO-(CH_2)_3-Si(OCH_3)_3$ from Hüls AG, Marl

Example 7: VTMO $H_2C=CH-Si(OCH_3)_3$ from Hüls AG, Marl

Example 8:

$$H_2C\underset{\diagdown O \diagup}{\overset{}{-\!\!-\!\!-}}CH-CH_2-O(CH_2)_3-Si(OC_2H_3)_3$$

from Hüls AG, Marl

Example 9: IMEO $$\begin{array}{c}H_2C-N-(CH_2)_3-Si(OC_2H_5)_3\\H_2C\diagdown\phantom{N}\diagup CH\\N\end{array}$$

from Hüls AG, Marl

Example 10: AMMO $H_2N-(CH_2)_3-Si(OCH_3)_3$ from Hüls AG, Marl

The pH is then brought to 7.2 with 32% sodium hydroxide solution, followed by further stirring for 15 minutes at 75° C. The suspension is then allowed to settle.

In Examples 6–10, clear differences in sedimentation are found:

Example 6: Pigment appears to be voluminous, settles slowly.

Example 7: Pigment settles relatively fast.

Example 8: Pigment settles similarly to Example 7.

Example 9: Pigment settles more slowly than in Examples 7 and 8, but better than in Example 6.

Example 10: Pigment settles similarly to Example 9.

The working-up of the 5 pigments (Examples 6–10) is carried out analogously to Example 3.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

We claim:

1. A pigment containing carbon black, comprising a platelet-shaped substrate coated with a metal oxide layer containing carbon black, wherein the carbon black is fixed on the substrate by means of an anionic or cationic and a nonionic surfactant and an organosilane compound.

2. A pigment containing carbon black, comprising a platelet-shaped substrate coated with a metal oxide layer containing carbon black doped with (1) an anionic or cationic surfactant, (2) a nonionic surfactant and (3) an organosilane compound.

3. A pigment according to claim 2, wherein the substrate is a platelet-shaped material coated with at least one metal oxide.

4. A pigment according to claim 2, wherein the platelet-shaped material is mica.

5. A pigment according to claim 2, wherein the amount of carbon black proportional to the total pigment is 0.1 to 10 by weight.

6. A pigment according to claim 2, wherein the anionic surfactant is a sulphonate.

7. A pigment according to claim 2, wherein the cationic surfactant is a quaternary ammonium compound.

8. A pigment according to claim 2, wherein the nonionic surfactant is an alcohol ethoxylate.

9. A pigment according to claim 2, wherein the organosilane compound is a compound of the formula

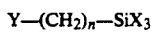

in which
Y is $H_2N-$, $H_2C=CH-$,

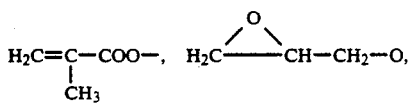

or 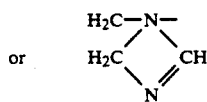

X is OR, Cl, or $-O-CO-CH_3$,
R is alkyl having 1-6 C atoms and
n is 0-3.

10. A pigment according to claim 9, wherein the organosilane compound is an amino silane.

11. A pigment according to claim 9, wherein the organosilane compound is

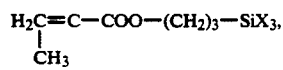

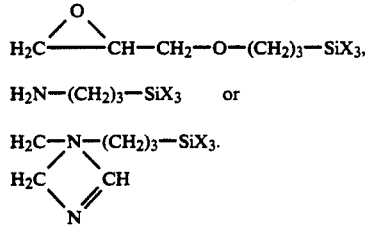

12. In a paint, dye, plastic or cosmetic comprising a carbon black containing pigment, the improvement wherein the pigment is one according to claim 1.

13. In a paint, dye, plastic or cosmetic comprising a carbon black containing pigment, the improvement wherein the pigment is one according to claim 2.

14. A process for the preparation of a pigment containing carbon black, comprising adding to an aqueous suspension of a platelet-shaped substrate
(i)
   (a) a hydrolyzable metal salt solution,
   (b) a carbon black dispersion containing an anionic or cationic surfactant,
   (c) a carbon black dispersion containing a nonionic surfactant, and
   (d) an organosilane compound;
(ii)
   (a) a hydrolyzable metal salt solution,
   (b) a carbon black dispersion containing an anionic or cationic surfactant,
   (c) an aqueous solution containing a nonionic surfactant, and
   (d) an organosilane compound; or
(iii)
   (a) a hydrolyzable metal salt solution,
   (b) a carbon black dispersion containing a nonionic surfactant,
   (c) an aqueous solution containing an anionic or cationic surfactant, and
   (d) an organosilane compound;
during which addition of the pH of the substrate suspension is maintained in a range causing hydrolysis of the metal salt and wherein optionally further hydrolysis of metal salt without readdition of carbon black is conducted, and the coated substrate is optionally separated off, washed, dried and calcined.

15. A process according to claim 14, wherein (a), (b), (c), and (d) are added simultaneously.

16. A process according to claim 14, wherein (a) is added simultaneously with at least one carbon black dispersion.

17. A pigment prepared by the process of claim 15.

18. A pigment prepared by the process of claim 16.

* * * * *